US011911313B2

(12) United States Patent
Brockman et al.

(10) Patent No.: US 11,911,313 B2
(45) Date of Patent: Feb. 27, 2024

(54) DEVICE FOR SECURING ADDITIONAL DEVICES IN AN EYE WITHOUT INTERFERING WITH VISION

(71) Applicant: Brockman-Hastings LLC, Lexington, KY (US)

(72) Inventors: Edward Britt Brockman, Louisville, KY (US); Jeffrey Todd Hastings, Lexington, KY (US); Carlos Andres Jarro, Lexington, KY (US); James L. Russell, Lexington, KY (US)

(73) Assignee: Brockman-Hastings LLC, Lexington, KY (US)

( * ) Notice: Subject to any disclaimer, the term of this patent is extended or adjusted under 35 U.S.C. 154(b) by 551 days.

(21) Appl. No.: 17/139,205

(22) Filed: Dec. 31, 2020

(65) Prior Publication Data

US 2021/0298946 A1  Sep. 30, 2021

Related U.S. Application Data

(60) Provisional application No. 63/002,428, filed on Mar. 31, 2020.

(51) Int. Cl.
| | | |
|---|---|---|
| *A61F 9/00* | (2006.01) | |
| *A61B 5/145* | (2006.01) | |
| *A61B 3/16* | (2006.01) | |
| *A61B 5/00* | (2006.01) | |
| *A61B 3/02* | (2006.01) | |

(52) U.S. Cl.
CPC .............. *A61F 9/0017* (2013.01); *A61B 3/02* (2013.01); *A61B 3/16* (2013.01); *A61B 5/14503* (2013.01); *A61B 5/14546* (2013.01); *A61B 5/6821* (2013.01); *A61B 5/6839* (2013.01); *A61B 5/6882* (2013.01)

(58) Field of Classification Search
CPC ......... A61B 3/02; A61B 3/16; A61B 5/14503; A61B 5/14546; A61B 5/6821; A61B 5/6839; A61B 5/6882; A61F 9/0017; A61F 2/16; A61F 2/1694; A61F 2002/1681; A61F 2002/1683; A61F 9/00781; A61F 2250/0001; A61F 9/0008
See application file for complete search history.

(56) References Cited

U.S. PATENT DOCUMENTS

| | | |
|---|---|---|
| 2003/0033014 A1 | 2/2003 | Gwon et al. |
| 2012/0004528 A1 | 1/2012 | Li et al. |
| 2012/0290086 A1 | 11/2012 | Malyugin et al. |
| 2018/0035888 A1* | 2/2018 | Irazoqui ................. A61B 5/686 |
| 2018/0132998 A1 | 5/2018 | Page |
| 2019/0321219 A1 | 10/2019 | Ostermeier et al. |

FOREIGN PATENT DOCUMENTS

WO    WO-2019038689 A1 *  2/2019  ........... A61F 9/0017

* cited by examiner

*Primary Examiner* — Eric J Messersmith
(74) *Attorney, Agent, or Firm* — Warren D. Schickli; Stites & Harbison, PLLC

(57) ABSTRACT

An eye implantation device has a body including a support system adapted to engage at three points with an irido-corneal angle of an anterior chamber of an eye into which the device is implanted.

15 Claims, 13 Drawing Sheets

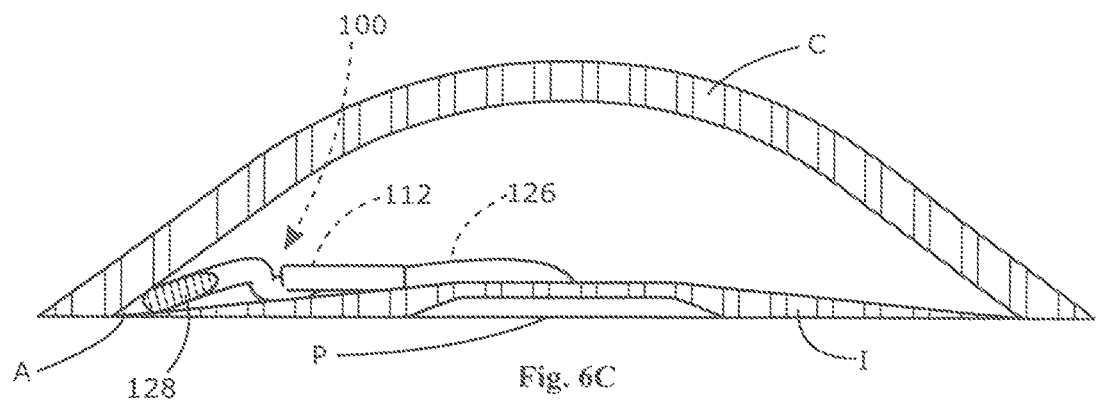
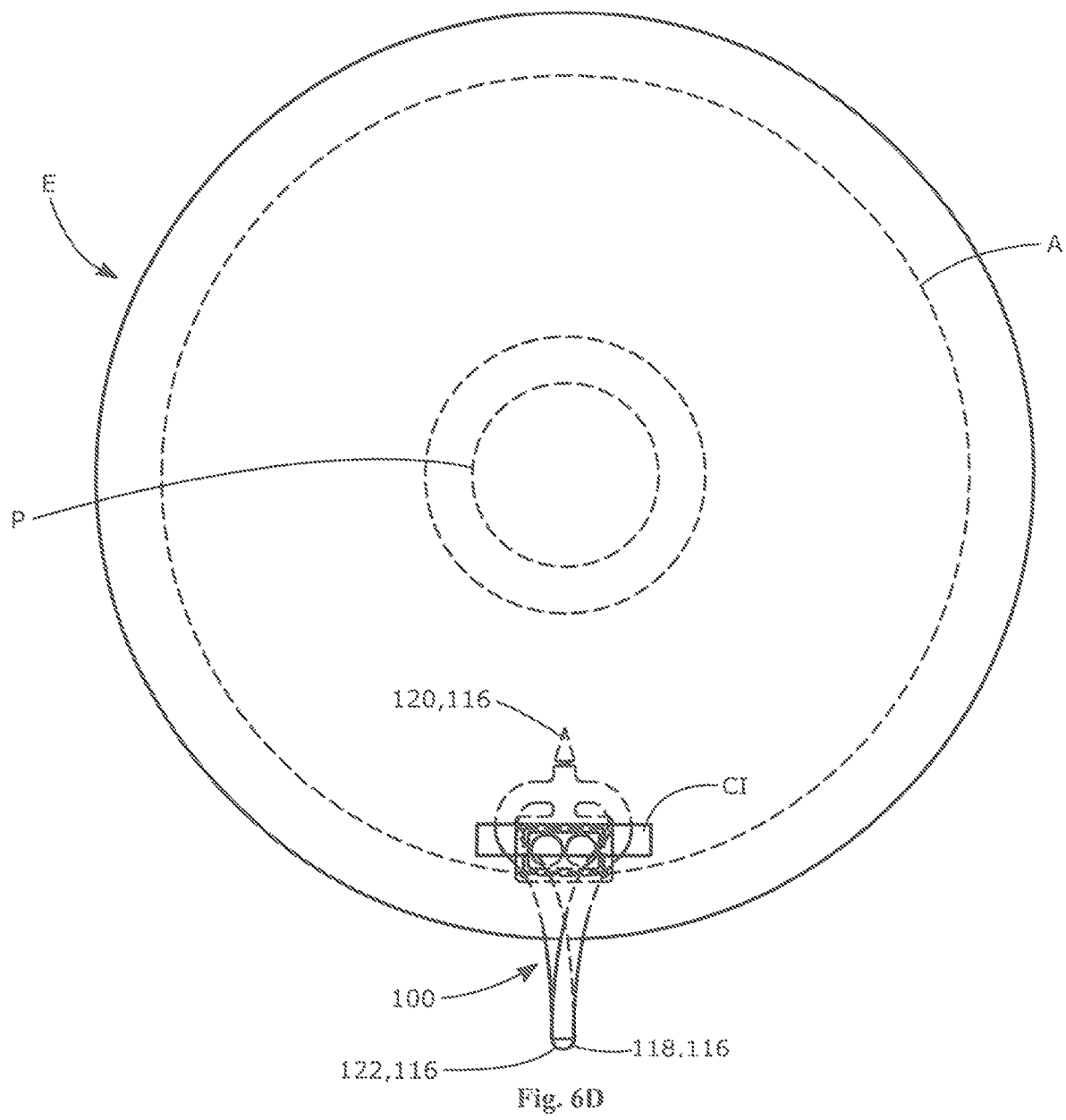

DEVICE FOR SECURING ADDITIONAL DEVICES IN AN EYE WITHOUT INTERFERING WITH VISION

RELATED APPLICATION

This application claims priority to U.S. Provisional patent application Ser. No. 63/002,428 filed on Mar. 31, 2020 which is hereby incorporated by reference in its entirety.

GOVERNMENT SUPPORT

This invention was made with an award from the Kentucky Cabinet for Economic Development, under Grant Agreement CED 2019-001-004.

TECHNICAL FIELD

This document relates generally to eye implants and, more particularly, to a new and improved eye implantation device adapted for receiving an intraocular device and holding that intraocular device at a desired position within the eye of a patient as well as to a related implantation method.

BACKGROUND

Various intraocular devices have been developed for in situ placement in the eye in order to (a) monitor chemical and physical characteristics in the eye related to eye diseases and medical conditions and/or (b) treat those eye diseases and medical conditions. Such intraocular devices include, but are not necessarily limited to (1) physical sensors for monitoring force, pressure, acceleration, etc., (2) chemical sensors for monitoring oxygen, glucose, amino acids, electrolytes, antigens, antibodies, etc., (3) miniature cameras, (4) drug delivery systems, (5) fluid pumps and (6) combinations thereof.

Such eye diseases and medical conditions include, but are not necessarily limited to glaucoma, cataracts, diabetes, strabismus and macular degeneration.

This document relates to a new and improved eye implantation device configured to receive and hold an intraocular device of the type described above at a desired position within the eye of a patient as well as to a related implantation method.

SUMMARY

In accordance with the purposes and benefits described herein, a new and improved eye implantation device is provided. That eye implantation device comprises a body including a support system adapted to engage at three points with an iridocorneal angle of an anterior chamber of the eye into which the eye implantation device is implanted. The eye implantation device further includes a receiver, on the body, adapted to receive and hold an intraocular device.

The intraocular device held in the receiver may be selected from a group consisting of a physical sensor (force, pressure, acceleration, etc.), a chemical sensor (oxygen, glucose, amino acids, electrolytes, antigens, antibodies, etc.), a miniature camera, a drug delivery system, a transceiver (optical, electromagnetic, ultrasonic, etc.), a fluid pump, and combinations thereof.

In one or more of the many possible embodiments of the eye implantation device, the support system includes a first support, a second support and a third support. The first support, the second support and the third support may be substantially provided on a common arc. That common arc may have a radius of curvature of between about 5.2 to 7.2 mm. That common arc may have a spread of between about 20-350 degrees.

In one or more of the many possible embodiments of the eye implantation device, at least one of the first, second and third supports is a barb. In some embodiments, the second support, provided on the common arc between the first support and the third support is the barb.

In one or more of the many possible embodiments of the eye implantation device, the body includes a first flexible wing. The first support may be provided at a distal end of the first flexible wing. In at least some of those embodiments, the body includes a second flexible wing. The third support may be provided at a distal end of the second flexible wing.

In one or more of the many possible embodiments of the eye implantation device, the body defines a chord of the common arc.

In one or more of the many possible embodiments of the eye implantation device, the first flexible wing substantially extends along the common arc from the first support to the second support. The second flexible wing may substantially extend along the common arc from the second support to the third support.

In one or more of the many possible embodiments of the eye implantation device, the first flexible wing forms a first S-curve and the second flexible wing forms a second S-curve.

In one or more of the many possible embodiments of the eye implantation device, the receiver may be located adjacent the second support within the common arc.

In one or more of the many possible embodiments of the eye implantation device, the common arc is substantially centered upon an optical axis of the eye in which the eye implantation device is implanted.

In accordance with an additional aspect, the eye implantation device comprises a body having (a) a receiver configured to hold an intraocular device and (b) a barb configured to engage with an iridocorneal angle of an anterior chamber of the eye into which the eye implantation device is implanted. That body may further include a first flexible wing and a second flexible wing.

In one or more of the many possible embodiments of the eye implantation device, the barb and the supports are located on a common arc. That common arc may have a radius of curvature of between about 5.2 to 7.2 mm. That common arc may have a spread of between about 20-350 degrees.

In accordance with yet another aspect, a method is provided for implanting an eye implantation device into an eye. That method comprises the steps of: (a) making a corneal incision of the eye, (b) inserting the eye implantation device into the eye through the corneal incision and (c) securing the eye implantation device by engaging the eye implantation device at three points with an iridocorneal angle of an anterior chamber of the eye into which the eye implantation device is implanted. The corneal incision may be a clear corneal incision of the type used for cataract surgery or of the type used for minimally invasive glaucoma surgery.

In one or more of the many possible embodiments of the method, the method further includes the step of positioning the eye implantation device within the eye so that the eye implantation device does not cross an 8 mm diameter circle centered on a pupil of the eye into which the eye implantation device is implanted.

In one or more of the many possible embodiments of the method, the method further includes the step of positioning the eye implantation device within the eye so as to be concealed behind an eyelid of the eye when the eyelid is in an open and relaxed state. Still further, the method may include selecting the intraocular device from a group of intraocular devices consisting of an intraocular pressure sensor, a miniature camera, a drug delivery system, an oxygen concentration sensor, an eye chemistry sensor and combinations thereof.

In one or more of the many possible embodiments of the method, the method further includes the step of positioning an intraocular device in a receiver of the eye implantation device prior to inserting of the eye implantation device into the eye through the corneal incision.

In one or more of the many possible embodiments of the method, the method further includes the step of selecting the intraocular device from a group of intraocular devices consisting of an intraocular pressure sensor, a miniature camera, a drug delivery system, an oxygen concentration sensor, an eye chemistry sensor and combinations thereof.

In one or more of the many possible embodiments of the method, the method further includes the step of folding the eye implantation device when inserting the eye implantation device into the eye through the corneal incision. Further, the method may include the step of holding the folded eye implantation device in a carrier during inserting the eye implantation device into the eye through the corneal incision and removing the eye implantation device from the carrier following insertion into the eye.

In accordance with yet another aspect, a new and improved method of implanting an eye implantation device into the eye comprises the steps of: (a) making a corneal incision of the eye, (b) inserting the eye implantation device into the eye through the corneal incision and (c) securing the eye implantation device by engaging a barb of the eye implantation device with an iridocorneal angle of an anterior chamber of the eye into which the eye implantation device is implanted. The corneal incision may be a clear corneal incision of the type used for cataract surgery or of the type used for minimally invasive glaucoma surgery.

In one or more of the many possible embodiments of the method, the method further includes the step of engaging additional supports of the eye implantation device with the iridocorneal angle of the anterior chamber of the eye wherein the barb and the additional supports are substantially located on a common arc.

In one or more of the many possible embodiments of the method, the method further includes the step of positioning the eye implantation device within the eye so that the eye implantation device does not cross an 8 mm diameter circle centered on a pupil of the eye into which the eye implantation device is implanted.

In one or more of the many possible embodiments of the method, the method further includes the step of positioning the eye implantation device within the eye so as to be concealed behind an eyelid of the eye when the eyelid is in an open and relaxed state.

In one or more of the many possible embodiments of the method, the method further includes the step of positioning an intraocular device in a receiver of the eye implantation device prior to inserting of the eye implantation device into the eye through the corneal incision.

In one or more of the many possible embodiments of the method, the method further includes the step of selecting the intraocular device from a group of intraocular devices consisting of an intraocular pressure sensor, a miniature camera, a drug delivery system, an oxygen concentration sensor, an eye chemistry sensor and combinations thereof.

Further, the method may include the step of folding the eye implantation device when inserting the eye implantation device into the eye through the corneal incision. Still further, the method may include the step of holding the folded eye implantation device in a carrier during inserting the eye implantation device into the eye through the corneal incision and removing the eye implantation device from the carrier following insertion into the eye.

In the following description, there are shown and described several preferred embodiments of the eye implantation device and the related method of implanting an eye implantation device into the eye of an individual or patient. As it should be realized, the eye implantation device and method are capable of other, different embodiments and their several details are capable of modification in various, obvious aspects all without departing from the eye implant and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the patent specification, illustrate several aspects of the eye implantation device and the related method and together with the description serve to explain certain principles thereof.

FIGS. 6B and 6C are respective cross sectional views taken along lines 6B-6B and 6C-6C of FIG. 6A.

FIG. 6D illustrates how the eye implantation device illustrated in FIG. 6A-6C may be folded to pass through a corneal incision when implanting in the eye of a patient.

Figure 1A:
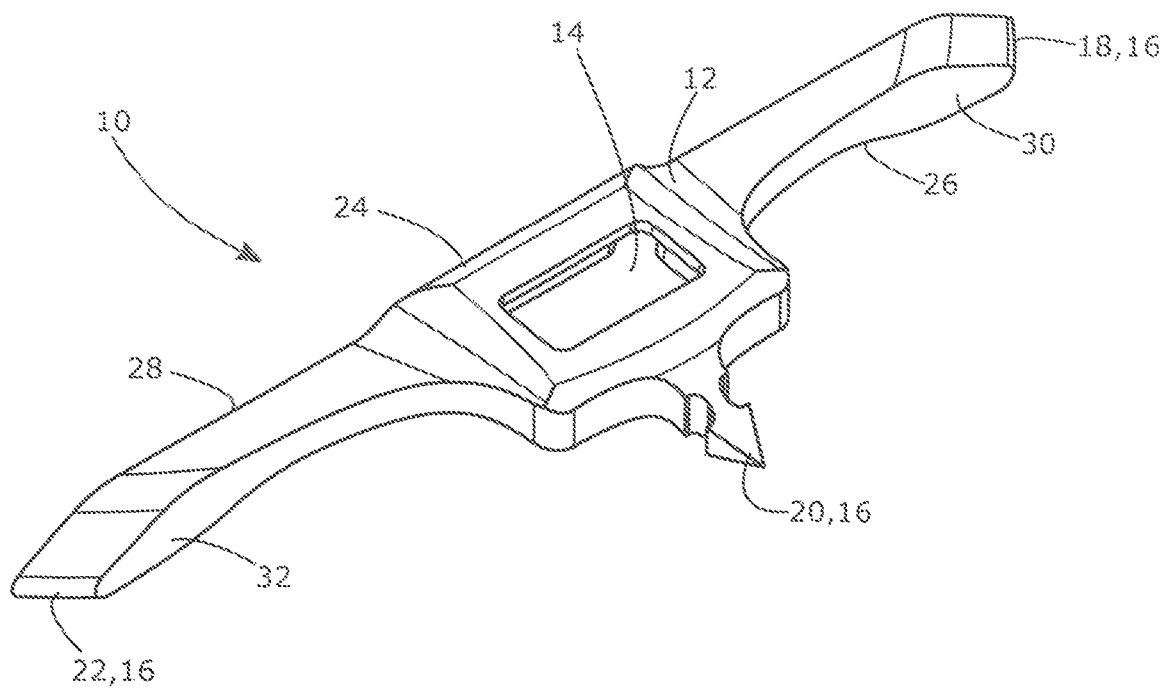
FIG. 1A is detailed perspective view of a first side of the new and improved eye implantation device.
Figure 1B:
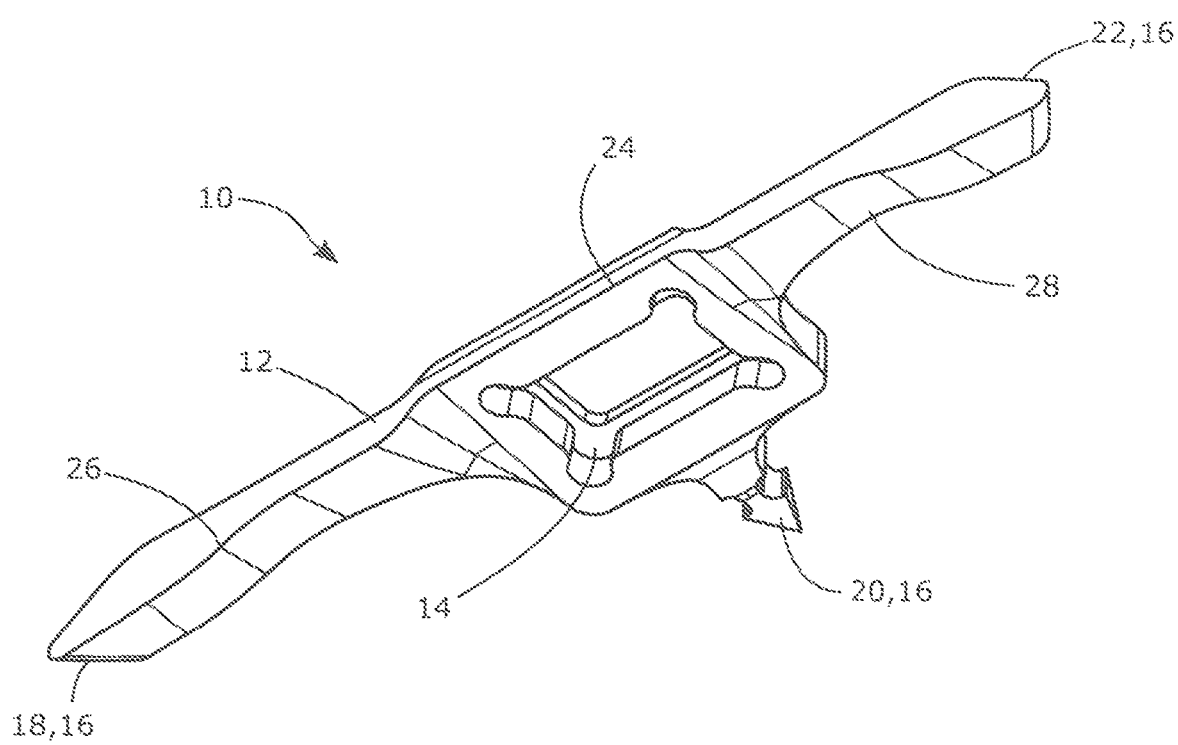
FIG. 1B is a perspective view of a second side of the eye implantation device illustrated in FIG. 1A.
Figure 1C:
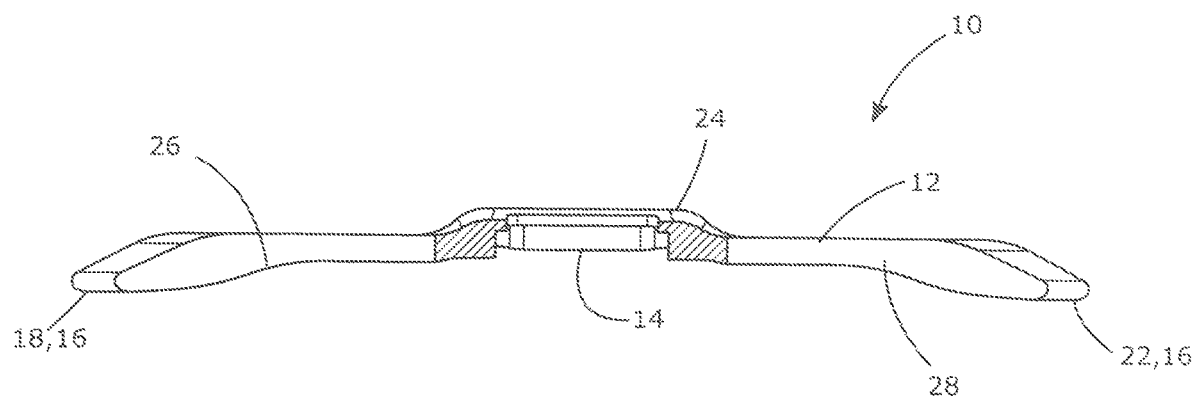
FIG. 1C is a partially cross-sectional view of the eye implantation device illustrated in FIGS. 1A and 1B.
Figure 1D:
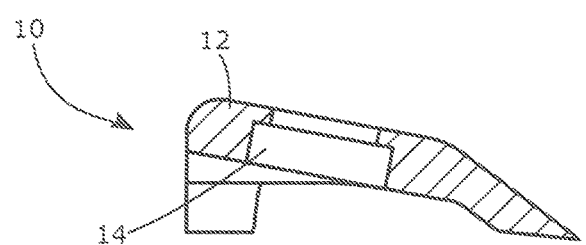
FIG. 1D is a cross sectional view of the eye implantation device illustrated in FIGS. 1A-1C.

Reference will now be made in detail to the present preferred embodiments of the eye implant and method, examples of which are illustrated in the accompanying drawing figures.

DETAILED DESCRIPTION

Reference is now made to FIGS. 1A-1D, 2A-2C, 3A, 3B, 4 and 5A-5B illustrating a first possible embodiment of the new and improved eye implantation device 10. The eye implantation device 10 includes a body 12 made from any appropriate biocompatible material. Such biocompatible material may be a biocompatible plastic, metal, metal alloy, plastic composite, ceramic or other material familiar to those skilled in the art. In one possible embodiment, the biocompatible material is a single piece of polymethylmethacrylate.

The body 12 may be vaulted to reduce contact between the body and the iris when implanted in the eye E. The dimensions of the body are also chosen to reduce contact with the cornea C and pupil P when implanted in the eye E. The outer edges of the body 12 may be rounded at the top to increase the clearance in the cornea C.

The body 12 includes a receiver 14 adapted or configured to hold an intraocular device D to be implanted in the eye of an individual or patient. More particularly, the receiver 14 may comprise a cavity, pocket or socket that is inset into the body 12. The receiver 14 may have one closed end. The interocular device D may comprise any of the various intraocular devices that have been developed for in situ placement in the eye E in order to (a) monitor chemical and physical characteristics in the eye related to eye diseases and medical conditions and/or (b) treat those eye diseases and medical conditions. Such intraocular devices D include, but are not necessarily limited to (1) a physical sensor for monitoring force, pressure, acceleration, etc., (2) a chemical sensor for monitoring oxygen, glucose, amino acids, electrolytes, antigens, antibodies, etc., (3) a miniature camera, (4) a drug delivery system, (5) a fluid pump and (6) combinations thereof. Such intraocular devices D include, but are not necessarily limited to an intraocular pressure sensor, a miniature camera, a drug delivery system, an oxygen concentration sensor, an eye motion sensor, an eye chemistry sensor, and combinations thereof.

The intraocular device D may be held in the receiver 14 by any appropriate means including, but not necessarily limited to, biocompatible adhesive, friction fit, interference fit, fasteners, bonding processes and combinations thereof.

The body 12 includes a support system, generally designated by reference numeral 16 that includes a first support 18, a second support 20 and a third support 22. The three supports 18, 20 and 22 are adapted to engage at three points with an iridocorneal angle A of an anterior chamber AC of an eye E of a patient into which the eye implantation device is implanted.

Figure 2A:
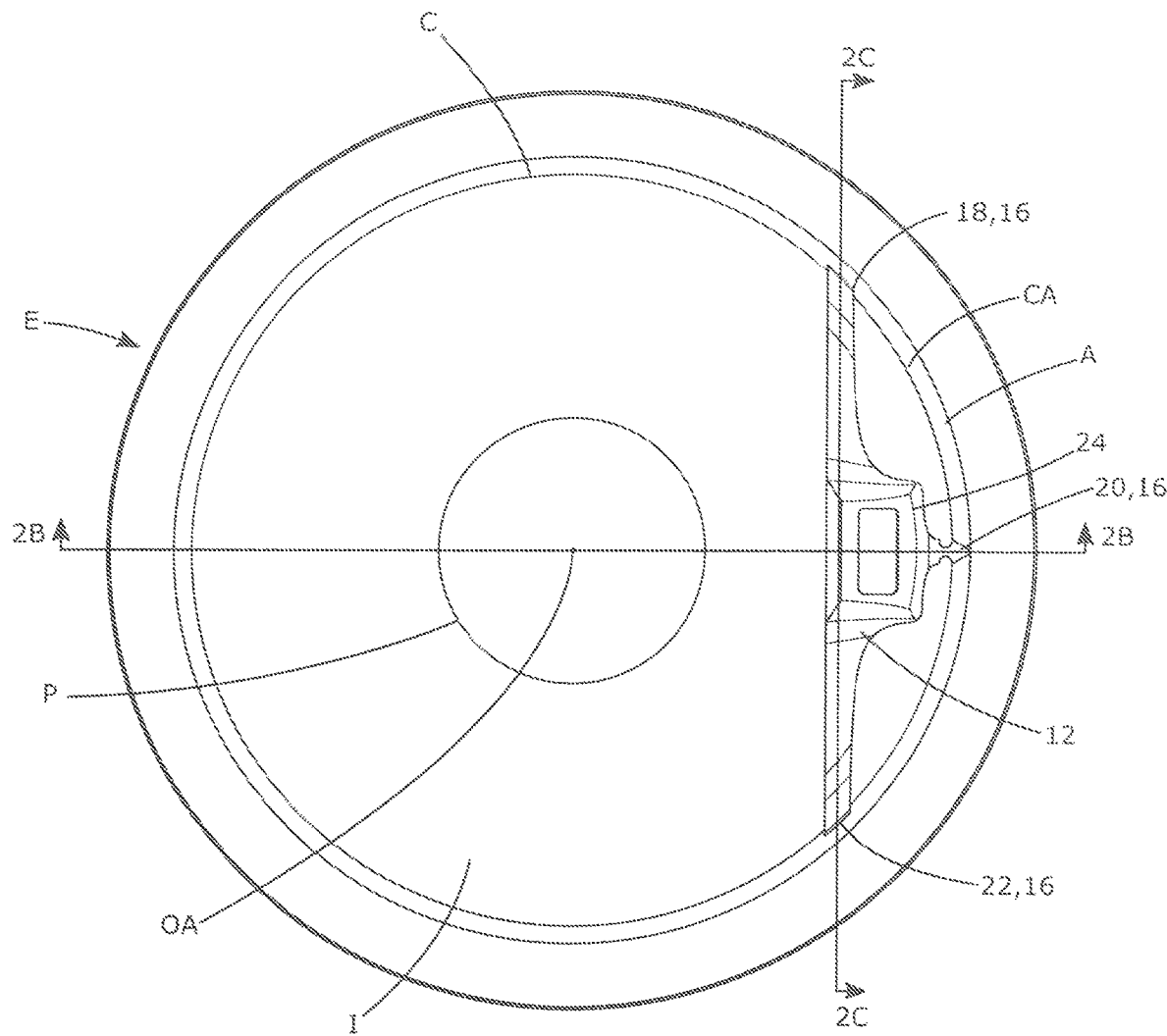
FIG. 2A is a front view of the eye implantation device illustrated in FIGS. 1A-1D implanted in an eye of a patient.
Figure 2B:
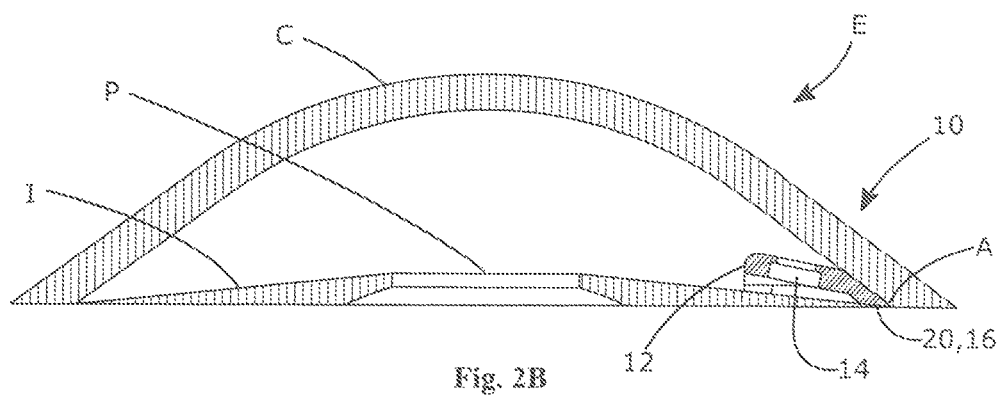
FIGS. 2B and 2C are two cross sectional views taken, respectively, along lines 2B-2B and 2C-2C of FIG. 2A.
Figure 2C:
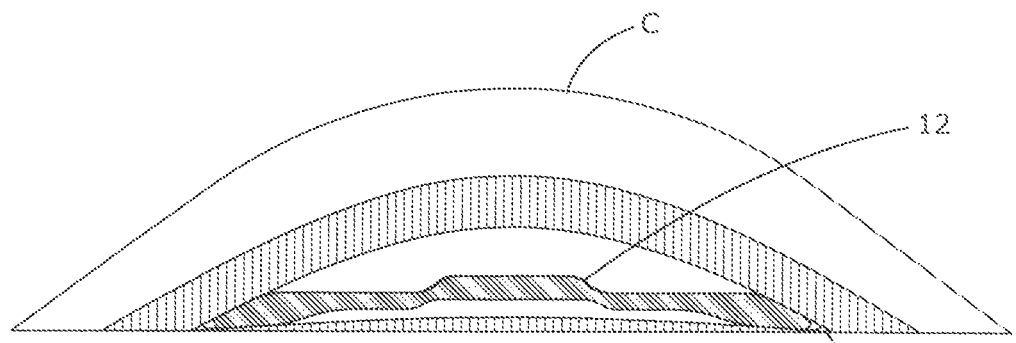

In the illustrated embodiment, the three supports 18, 20 and 22 are substantially provided on a common arc CA that has a radius of curvature of between about 5.2 to about 7.2 mm. As illustrated in FIG. 2A the common arc may substantially correspond to the arc of the iridocorneal angle A of the eye E into which the device 10 is implanted. Thus, when properly implanted, the common arc CA is substantially centered upon an optical axis OA of the eye E into which the eye implantation device 10 is implanted.

The common arc CA inscribed by the three supports 18, 20 and 22 of the support system 16 may have a spread of between about 20 to about 350 degrees. The receiver 14 is located adjacent the second support 20 within the common arc CA.

At least one of the three supports 18, 20 and 22 may be a barb. In the embodiment illustrated in FIGS. 1A-1D, 2A-2C, 3A, 3B, 4 and 5A-5B, the second support 20, provided on the common arc CA between the first support 18 and the third support 22 is the barb. The barb 20 penetrates the ocular tissue to secure the device 10 in place while the other supports 18 and 22 stabilize and prevent the device from moving, tilting or rotating in the eye and potentially contacting the cornea C by engaging the iridocorneal angle A on both sides of the barb. The device 10 does not interfere with light passing through the pupil of the eye E.

As should be appreciated, the body 12 includes a central portion 24, including the receiver 14, a first wing 26, extending in a first direction from the central portion and a second wing 28 extending from the central portion in a second direction. In the embodiment illustrated in FIGS. 1A-1D, 2A-2C, 3A, 3B, 4 and 5A-5B, the body 12, including the central portion 24, the first wing 26 and the second wing 28 substantially defines a chord of the common arc CA. It should be appreciated that the wings 26 and 28 can be made of flexible or rigid materials depending on the desired interface with the iridocorneal angle, the required clearance from the iris and the cornea, and the preferred biocompatible material.

The first support 18 is provided at the distal end 30 of the first wing. The second support 20 is provided on the central portion 24. The third support 22 is provided at the distal end 32 of the second wing 28.

Reference is now made to FIGS. 6A-6E illustrating a first alternative embodiment of the eye implantation device 100 where like reference numbers identify like structures to those described in detail above respecting the first embodiment illustrated in FIGS. 1A-1D, 2A-2C, 3A, 3B, 4 and 5A-5B. The device 100 includes a body 112 having a central portion 124 with a receiver 114 adapted to receive and hold an intraocular device D such as (1) a physical sensor for monitoring force, pressure, acceleration, etc., (2) a chemical sensor for monitoring oxygen, glucose, amino acids, electrolytes, antigens, antibodies, etc., (3) a miniature camera, (4) a drug delivery system, (5) a fluid pump and (6) combinations thereof. Such intraocular devices D include, but are not necessarily limited to an intraocular pressure sensor, a miniature camera, a drug delivery system, an oxygen concentration sensor, an eye motion sensor, an eye chemistry sensor, and combinations thereof.

Figure 6A:
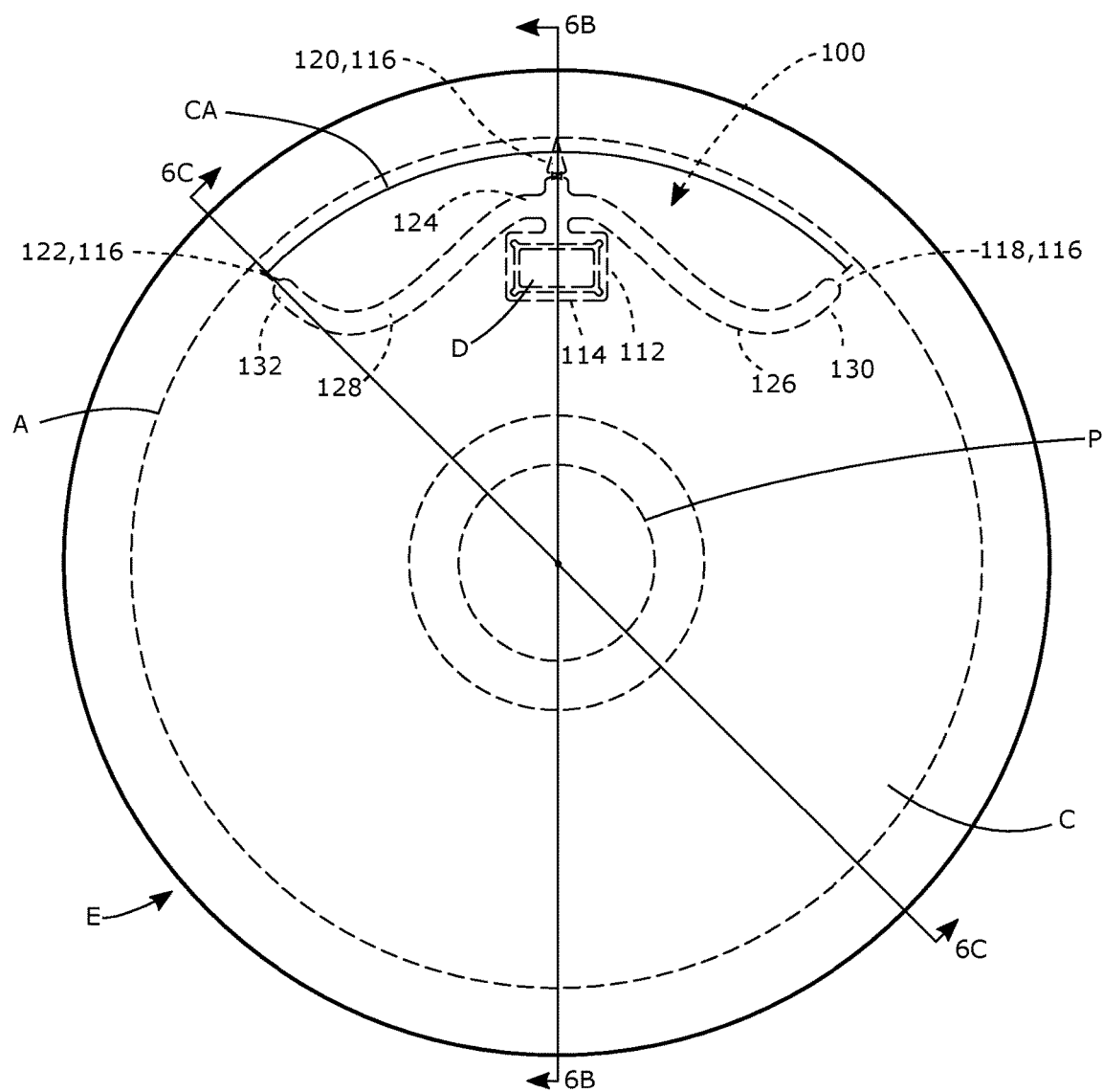
FIG. 6A is a front elevational illustrating an alternative embodiment of the eye implantation device implanted in the eye of the patient.
Figure 6B:
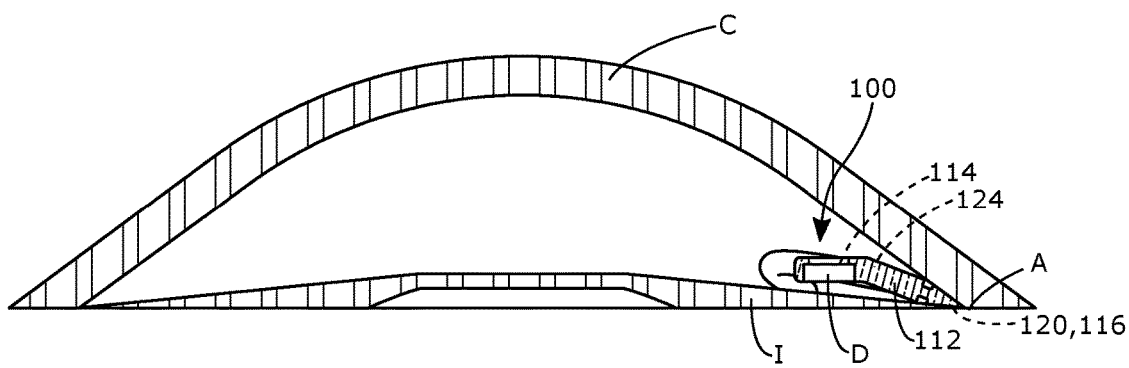
Figure 6E:
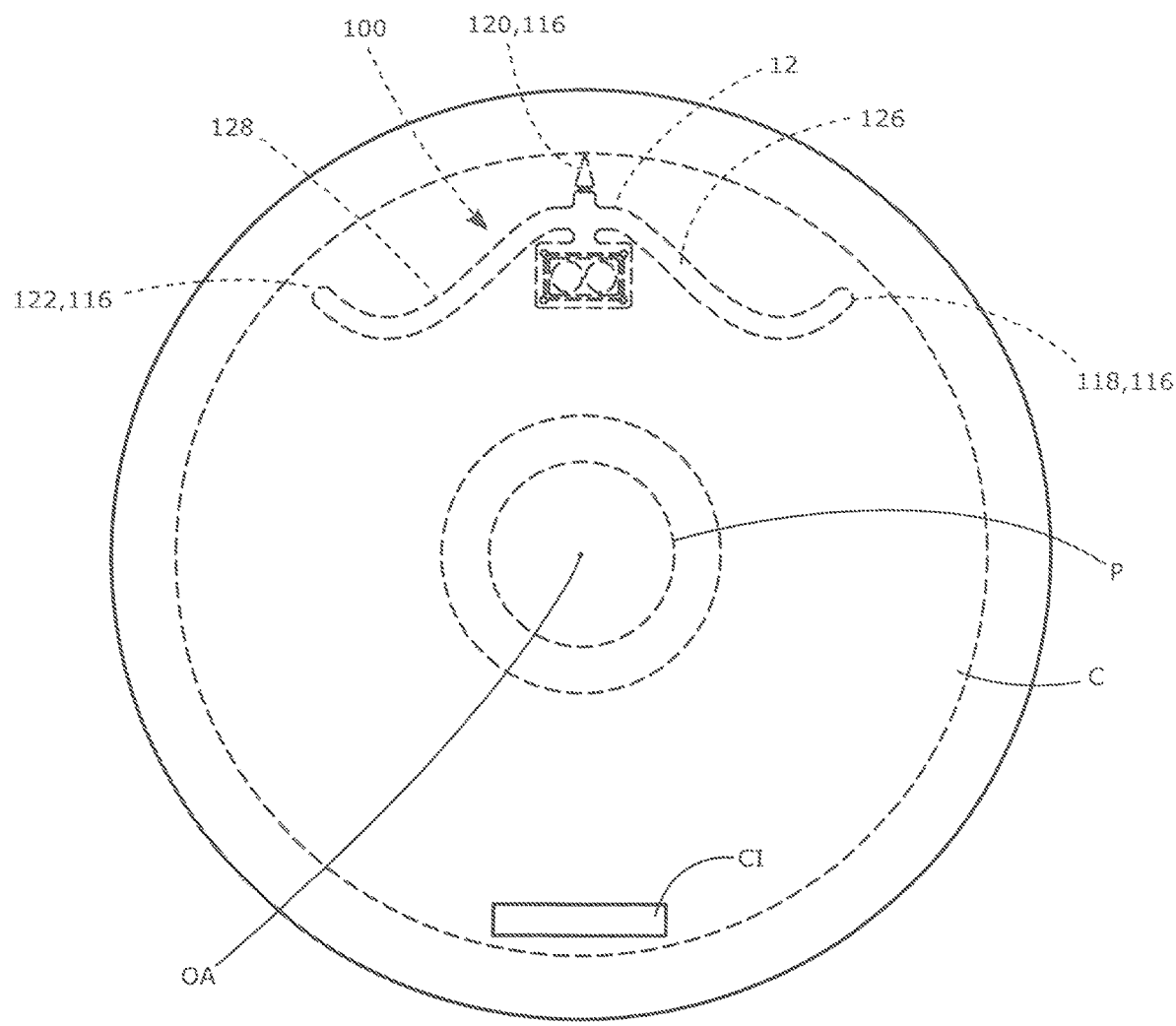
FIG. 6E illustrates the eye implantation device of FIGS. 6A-6C as it is being implanted.

The body 112 also includes a first flexible wing 126 and a second flexible wing 128 extending or projecting from the central portion 124. Unlike the first embodiment of the eye implantation device 10, the first flexible wing 126 of the second embodiment of the eye implantation device 100 forms a first S-curve and the second flexible wing 126 forms a second S-curve. The first support 118 is carried in the distal end 130 of the first flexible wing 126, the second support 120 is carried on the central portion 124 adjacent or near the receiver 114 and the third support 122 is carried on the distal end 132 of the second flexible wing 128. As shown in FIG. 6A, the first support 118, the second support 120 and the third support 122 are substantially provided on a common arc CA that substantially corresponds to the arc of the iridocorneal angle A of the eye E into which the device 100 is implanted.

Reference is now made to FIGS. 7A-7E illustrating a barbless embodiment of the eye implantation device 200 where like reference numbers identify like structures to those described in detail above respecting the first embodiment illustrated in FIGS. 1A-1D, 2A-2C, 3A, 3B, 4 and 5A-5B. The device 200 includes a body 212 having a central portion 224 with a receiver 214 adapted to receive and hold an intraocular device D such as (1) a physical sensor for monitoring force, pressure, acceleration, etc., (2) a chemical sensor for monitoring oxygen, glucose, amino acids, electrolytes, antigens, antibodies, etc., (3) a miniature camera, (4) a drug delivery system, (5) a fluid pump and (6) combinations thereof. Such intraocular devices D include, but are not necessarily limited to an intraocular pressure sensor, a miniature camera, a drug delivery system, an oxygen concentration sensor, an eye motion sensor, an eye chemistry sensor, and combinations thereof.

The body 212 also includes a first flexible wing 226 and a second flexible wing 228 extending or projecting from the central portion 224. Unlike the first embodiment of the eye implantation device 10, the first flexible wing 226 and the second flexible wing 228 of the third embodiment of the eye implantation device 200 span a much greater arc of about 250 degrees.

Figure 7A:
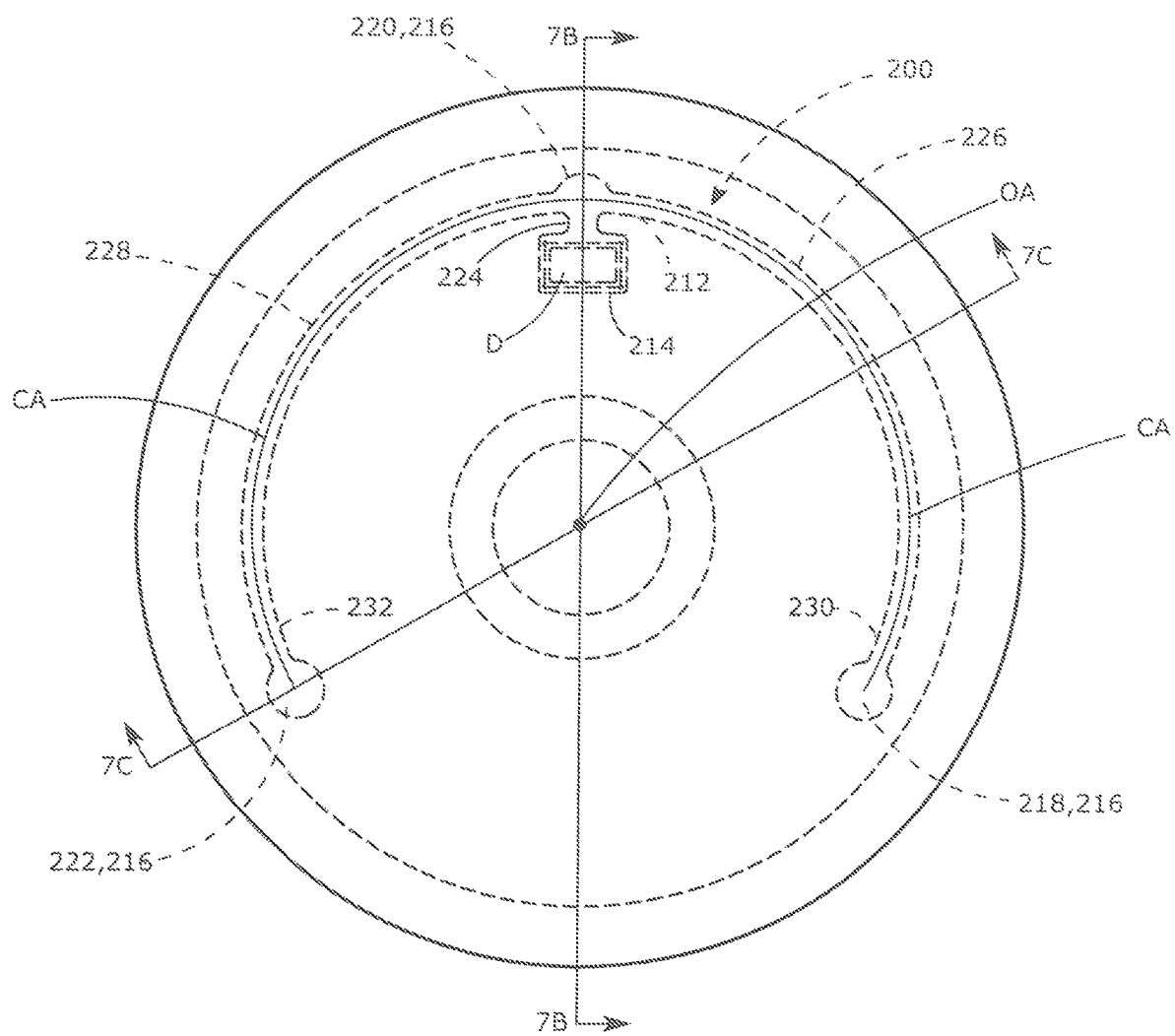
FIG. 7A is a front elevational view of yet another alternative embodiment of the eye implantation device shown implanted in the eye of a patient.
Figure 7B:
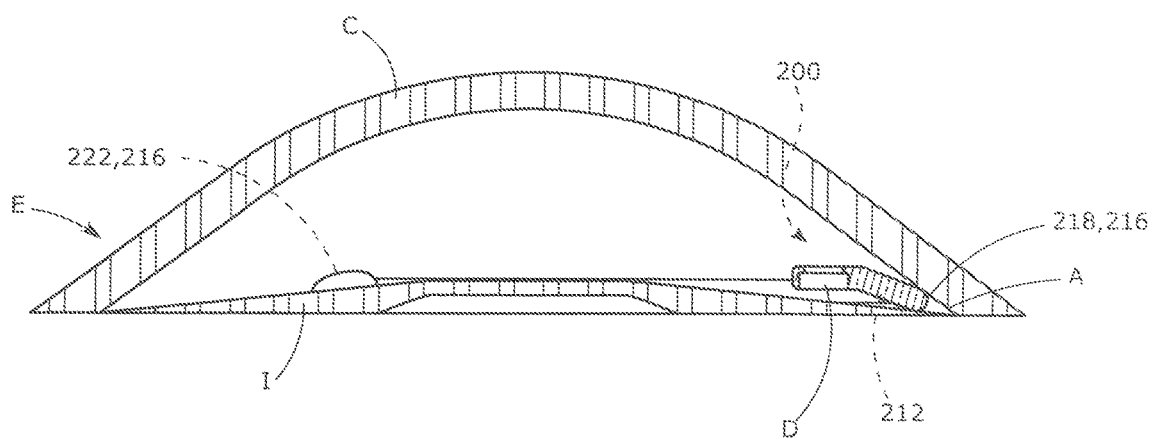
FIGS. 7B and 7C are respective cross sectional views taken along lines 7B-7B and 7C-7C of FIG. 7A.
Figure 7C:
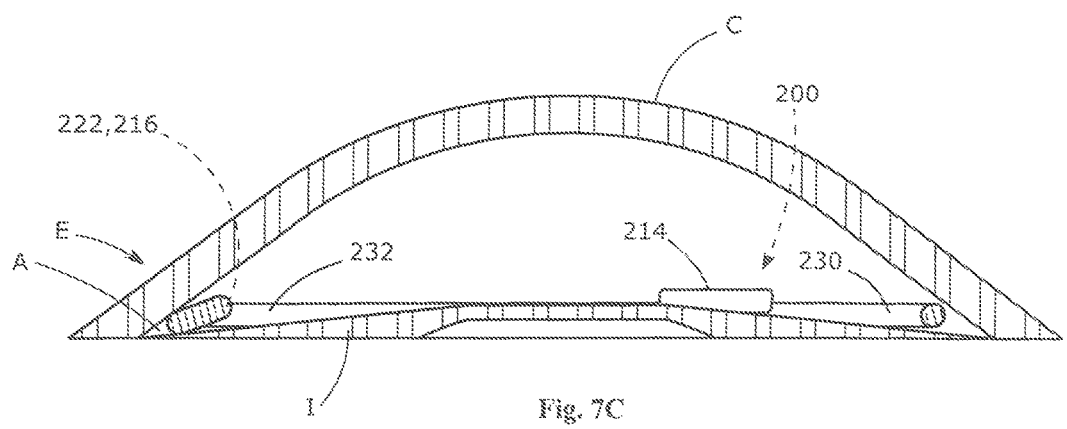

The first support 218 is carried in the distal end 230 of the first flexible wing 226, the second support 220 is carried on the central portion 224 adjacent or near the receiver 214 and the third support 222 is carried on the distal end 232 of the second flexible wing 228. As shown in FIG. 7A, the first support 218, the second support 220 and the third support 222 are substantially provided on a common arc CA that substantially corresponds to the arc of the iridocorneal angle A of the eye E into which the device 200 is implanted.

Figure 3A:
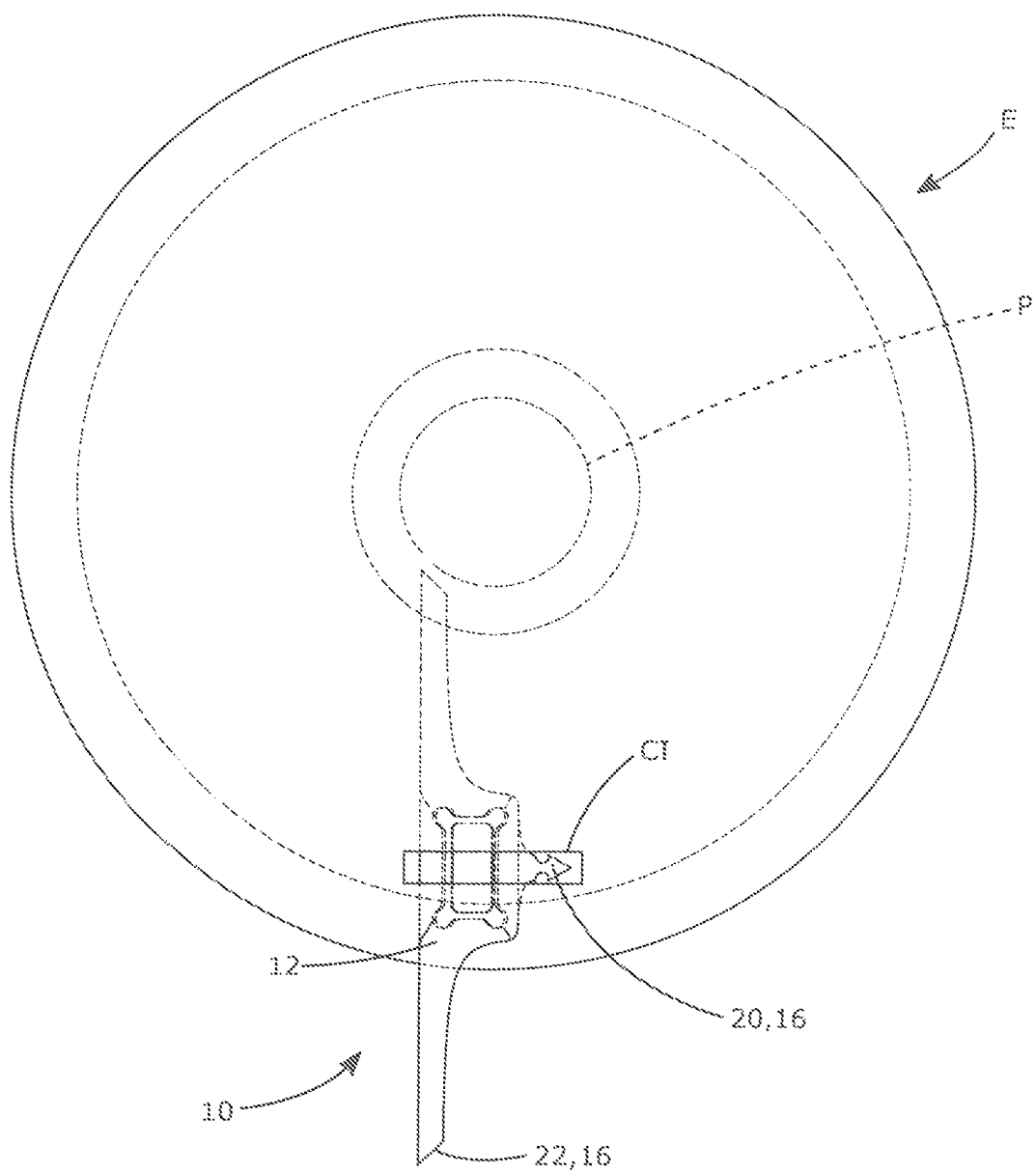
FIGS. 3A and 3B are views illustrating implantation of the eye implantation device into an eye of a patient.
Figure 3B:
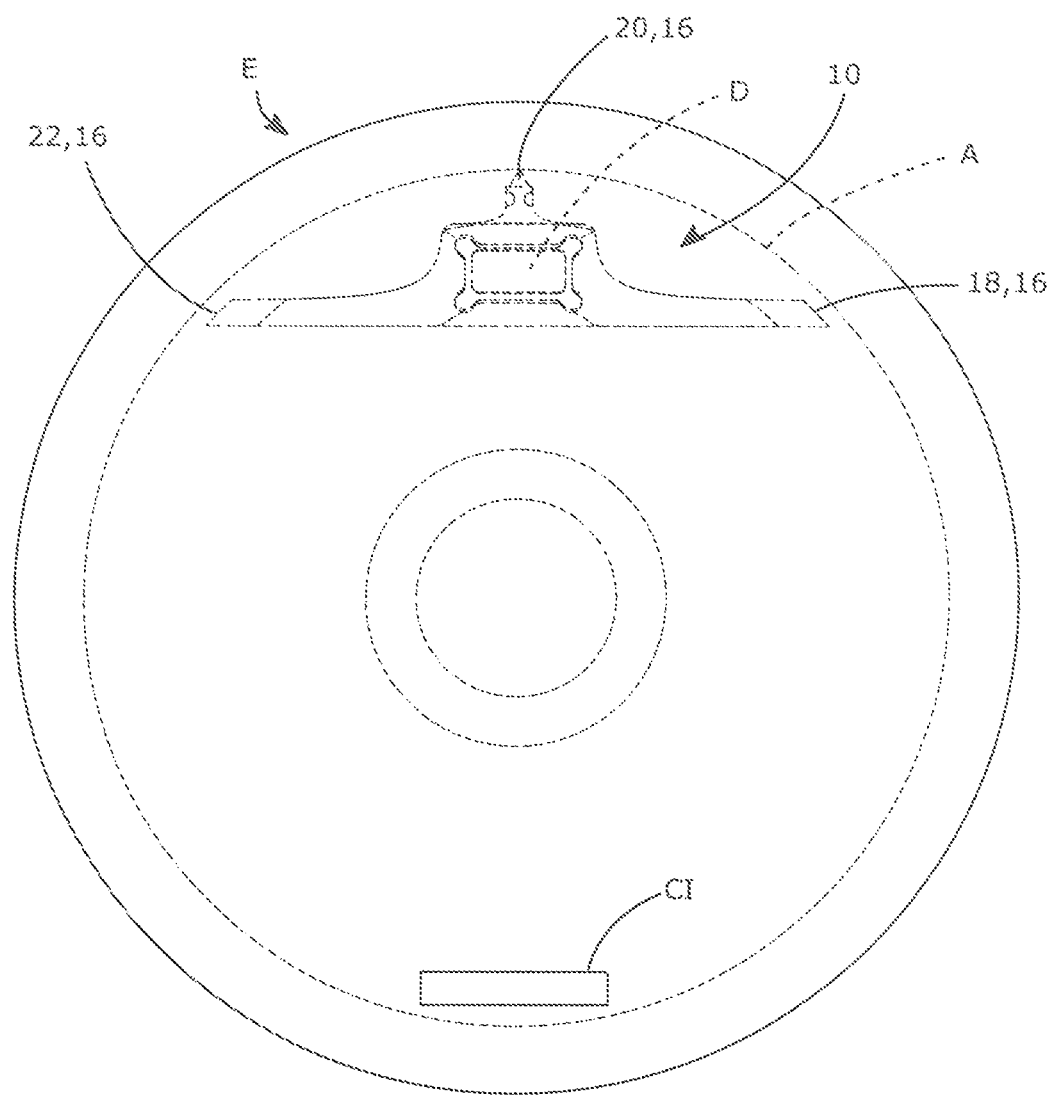
Figure 4:
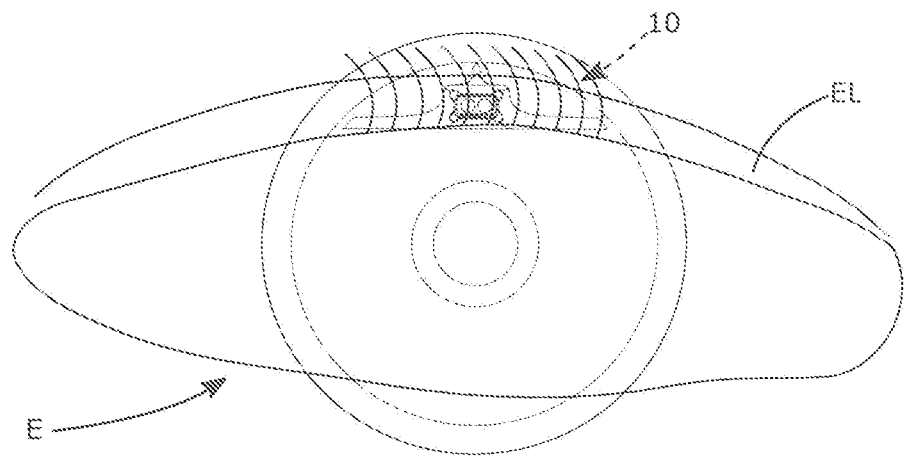
FIG. 4 is a view illustrating how a relaxed eye lid covers the eye implantation device when properly implanted into the eye of a patient.
Figure 5A:
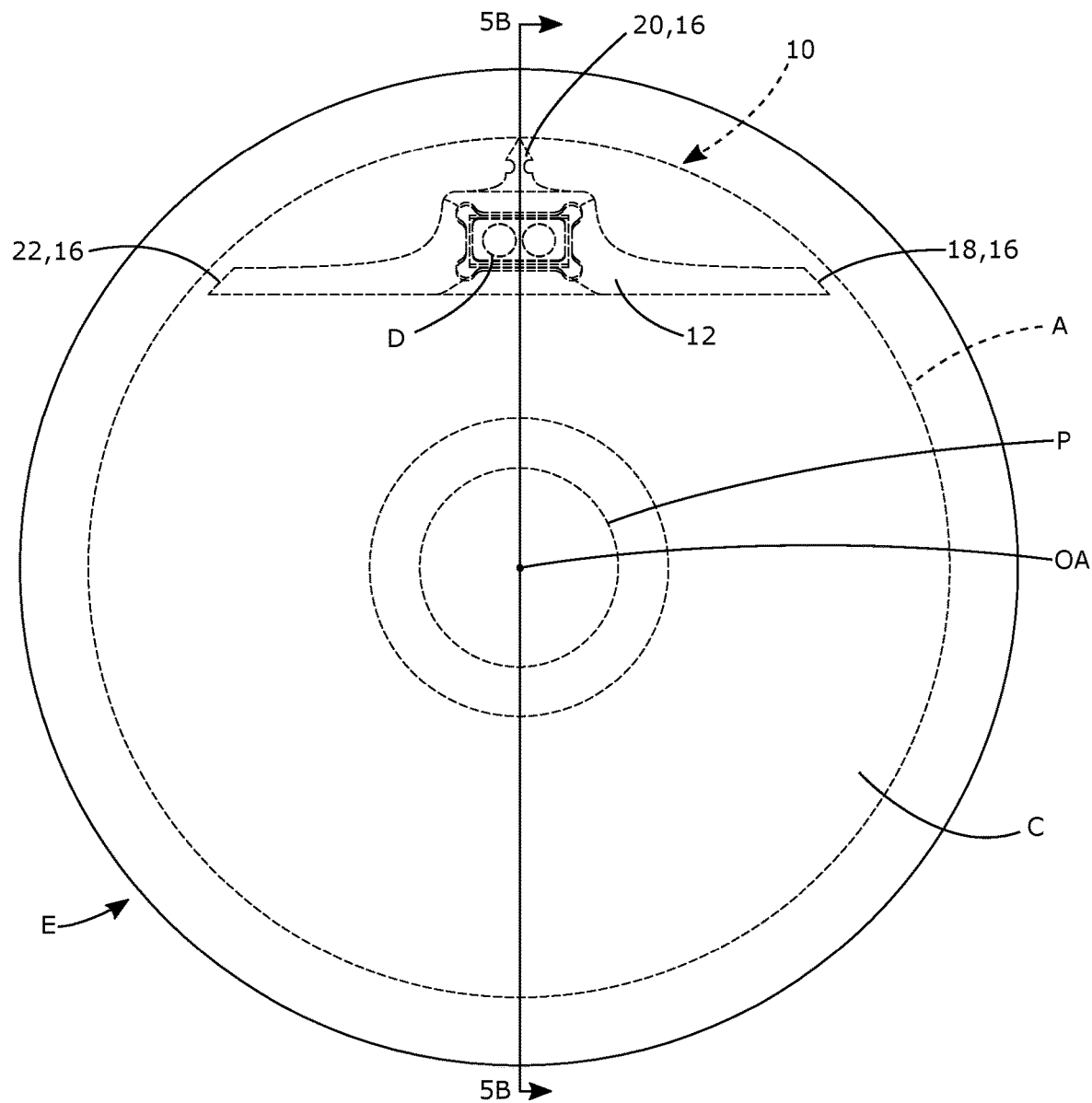
FIGS. 5A and 5B are respective front elevational and cross sectional views illustrating the eye implantation device implanted in the eye and holding an ocular device at a desired angle with respect to the cornea.
Figure 5B:
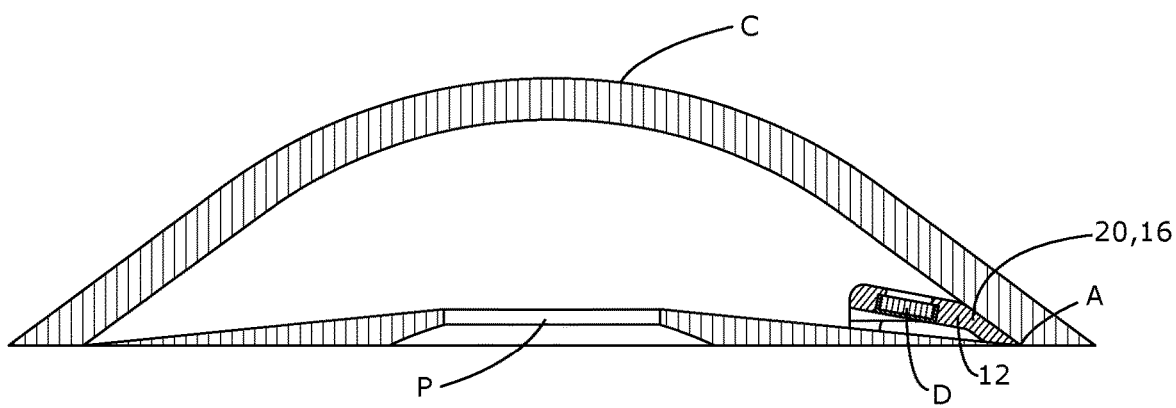

Reference is now made to FIGS. 3A-3B which illustrate the new and improved method of implanting an eye implantation device 10 into an eye E of an individual or patient. That method may be broadly described as including the steps of: (a) making a corneal incision CI of the eye E, (b) inserting the eye implantation device 10 into the eye through the corneal incision (see FIGS. 3A and 3B) and (c) securing the eye implantation device at three points with the iridocorneal angle A of the anterior chamber AC of the eye into which the eye implantation device is implanted. In the embodiment illustrated in FIGS. 3A-3C, this method more specifically includes securing the eye implantation device 10 by engaging a barb 20 of the eye implantation device with the iridocorneal angle A of the anterior chamber AC of the eye into which the eye implantation device 10 is implanted.

The corneal incision CI may be a clear corneal incision of the type used for cataract surgery or a clear corneal incision of the type used for minimally invasive glaucoma surgery. Advantageously, such a corneal incision CI does not require suturing for closure. FIG. 3A illustrates the eye implantation device 10 being implanted through the corneal incision CI into the anterior chamber AC of the eye E. The device 10 is sized to allow it to be rotated inside the anterior chamber AC and secured at a location dictated by the desired location of the intraocular device held in the receiver 14. As a result, the location of the incision can be chosen based upon surgical considerations including induced astigmatism and accessibility for the surgeon.

The method may include the step of positioning the eye implantation device 10 within the eye so that the eye implantation device does not cross an approximately 8 mm diameter circle (approximate pupil diameter at full dilation) centered on the pupil P of the eye into which the eye implantation device is implanted. As shown, when implanted in this manner, the eye implantation device 10 does not cross the pupil P of the eye E, thereby eliminating any need for an iridotomy or an iridectomy and not interfering with vision. Further, the method may include the step of positioning the eye implantation device 10 within the eye E so as to be substantially concealed behind an eyelid EL of the eye into which the eye implantation device is implanted. See FIG. 4.

The method may also include the step of positioning an intraocular device D in the receiver 14 of the eye implantation device 10 prior to inserting the eye implantation device into the eye E through the corneal incision CI. Further, the method may include the step of selecting the intraocular device from a group of intraocular devices consisting of an intraocular pressure sensor, a miniature camera, a drug delivery system, an oxygen concentration sensor, an eye chemistry sensor and combinations thereof.

Figure 7D:
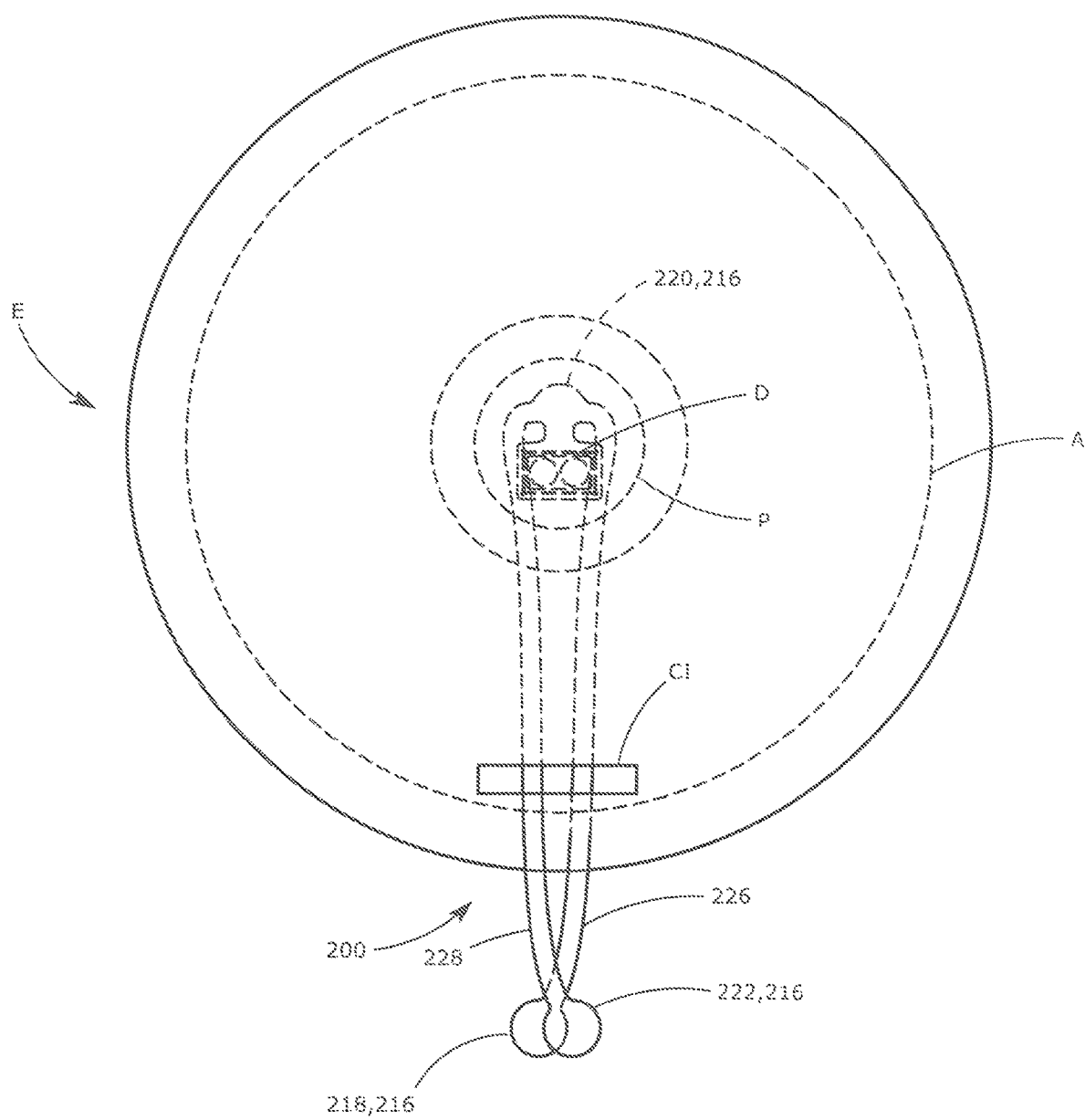
FIG. 7D illustrates how the eye implantation device illustrated in FIGS. 7A-7C may be folded to pass through a corneal incision when implanting in the eye of a patient.
Figure 7E:
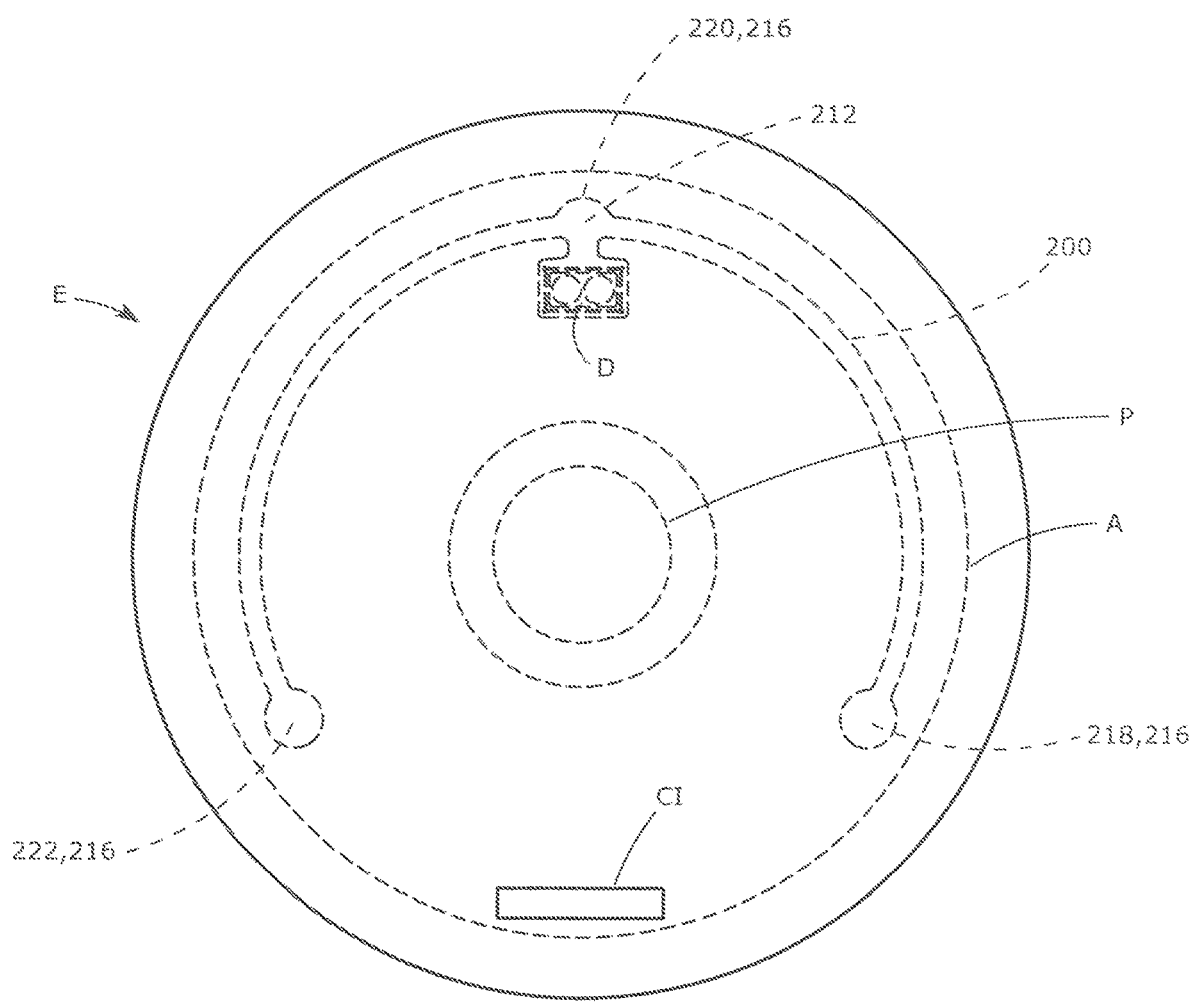
FIG. 7E illustrates the eye implantation device of FIGS. 7A-7C as it is being implanted.

As illustrated in FIGS. 6D and 7D, the method may also include the step of folding the eye implantation device 100 or 200 when inserting the eye implantation device into the eye through the corneal incision CI. More specifically, in the illustrated embodiments, it is the first and second flexible wings 126, 128 and 226, 228 that are folded to pass through the relatively small and narrow corneal incisions CI.

While not illustrated, it should be appreciated that the device 10, 100, 200 may be placed within a carrier such as a tube or injector when being inserted into the eye through the corneal incision CI.

A number of benefits and advantages are provided by the new and improved eye implantation device. These include but are not necessarily limited to the following. When properly implanted, the eye implantation device 10, 100, 200 does not cross the pupil P, thus it does not alter eyesight of the patient. The eye implantation device 10, 100, 200 does not contact the anatomy of the eye at symmetric points about the pupil P. The device 10, 100, 200 reduces contact with the cornea endothelium and iris I. The device 10, 100, 200 can be implanted through a small incision such as associated with clear corneal cataract surgery or minimally invasive glaucoma surgery. The device 10, 100, 200 can be folded or compressed to fit through a smaller incision. Further, the device 10, 100, 200 can be configured to rest under an eyelid EL to protect the device and/or improve aesthetics.

Each of the following terms written in singular grammatical form: "a", "an", and the", as used herein, means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of". Each of the phrases "consisting of and "consists of, as used herein, means "including and limited to". The phrase "consisting essentially of means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms concentric, parallel or perpendicular are meant to mean approximately meeting this condition, unless otherwise specified.

It is to be fully understood that certain aspects, characteristics, and features, of the eye implantation device and method, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the eye implantation device and method which are illustratively described and presented in combination or sub-combination in the context or format of a single embodiment may also be illustratively described and presented in the context or format of a plurality of separate embodiments.

Although the eye implantation device and method of this disclosure have been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The foregoing has been presented for purposes of illustration and description. It is not intended to be exhaustive or to limit the embodiments to the precise form disclosed. Obvious modifications and variations are possible in light of the above teachings. For example, the body 12, 112, 212 may include more than one receiver 14, 114, 214 for holding more than one intraocular device D. The (a) body 12, 112, 212 and (b) the wings 26, 28/126, 128/226, 228 may be made from a single piece of biocompatible material such as polymethylmethacrylate or they may be made from multiple pieces of the same or different materials. All such modifications and variations are within the scope of the appended claims when interpreted in accordance with the breadth to which they are fairly, legally and equitably entitled.

What is claimed is:

1. An eye implantation device, comprising a body including a support system adapted to engage at three points with an iridocorneal angle of an anterior chamber of the eye into which the eye implantation device is implanted wherein the support system includes a first support, a second support and a third support provided on a common arc and the second support, provided on the common arc between the first support and the third support is a barb.

2. The eye implantation device of claim 1, further including a receiver on the body adapted to receive an intraocular device.

3. The eye implantation device of claim 1, wherein the common arc has a radius of curvature of between about 5.2 to 7.2 mm.

4. The eye implantation device of claim 3, wherein the common arc has a spread of between about 20-350 degrees.

5. The eye implantation device of claim 1, wherein the body includes a first wing.

6. The eye implantation device of claim 5, wherein the first support is provided at a distal end of the first wing.

7. The eye implantation device of claim 6, wherein the body includes a second wing.

8. The eye implantation device of claim 7, wherein the second support is provided at a distal end of the second wing.

9. The eye implantation device of claim 8, wherein the body defines a chord of the common arc.

10. The eye implant of claim 8, wherein the first wing is flexible and forms a first S-curve and the second wing is flexible and forms a second S-curve.

11. The eye implant device of claim 8, wherein the first wing substantially extends along the common arc from the first support to the second support.

12. The eye implant of claim 11, wherein the second wing substantially extends along the common arc from the second support to the third support.

13. The eye implant device of claim 2, wherein the receiver is located adjacent the second support within the common arc.

14. The eye implantation device of claim 13, wherein the intraocular device is selected from a group consisting of physical sensors, chemical sensors, miniature cameras, drug delivery systems, transceivers, fluid pumps and combinations thereof.

15. The eye implantation device of claim 14, wherein the common arc is substantially centered upon an optical axis of the eye in which the eye implantation device is implanted.

* * * * *